(12) United States Patent
Brown et al.

(10) Patent No.: US 10,403,413 B2
(45) Date of Patent: Sep. 3, 2019

(54) BEAM FILTER ASSEMBLY AND BEAM FILTER POSITIONING DEVICE

(71) Applicant: Varian Medical Systems, Inc., Palo Alto, CA (US)

(72) Inventors: Christopher Brown, Morgan Hill, CA (US); Rachel Rieger, Redwood City, CA (US); Dusan Baic, Santa Clara, CA (US); Sean Kelley, Menlo Park, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 15/282,916

(22) Filed: Sep. 30, 2016

(65) Prior Publication Data

US 2018/0096746 A1    Apr. 5, 2018

(51) Int. Cl.
*G21K 1/10* (2006.01)
*A61B 6/00* (2006.01)

(52) U.S. Cl.
CPC ............... *G21K 1/10* (2013.01); *A61B 6/4035* (2013.01)

(58) Field of Classification Search
CPC ............... G21K 1/10; G21K 1/12; G21K 1/14
USPC ............................................. 250/505.1, 522.1
See application file for complete search history.

(56) References Cited

U.S. PATENT DOCUMENTS

| | | | | |
|---|---|---|---|---|
| 4,101,766 A | * | 7/1978 | Minami | G03B 42/023 378/158 |
| 5,864,146 A | * | 1/1999 | Karellas | A61B 6/06 250/581 |
| 6,148,062 A | * | 11/2000 | Romeas | G21K 1/04 378/156 |
| 2004/0000650 A1 | * | 1/2004 | Yanagisawa | A61N 5/1042 250/492.3 |
| 2004/0143177 A1 | * | 7/2004 | Falbo, Sr. | A61B 6/0442 600/407 |
| 2006/0109951 A1 | * | 5/2006 | Popescu | A61B 6/032 378/4 |
| 2008/0067452 A1 | * | 3/2008 | Moriyama | A61N 5/1048 250/503.1 |
| 2010/0260319 A1 | * | 10/2010 | Ein-Gal | A61N 5/1042 378/65 |
| 2011/0075810 A1 | * | 3/2011 | Sendai | A61B 6/4042 378/95 |
| 2014/0112441 A1 | * | 4/2014 | Becker | A61B 6/032 378/62 |

* cited by examiner

*Primary Examiner* — Jason L McCormack

(57) ABSTRACT

In a beam filter assembly, a base filter is employed to modify a beam quality of a radiation beam of a base energy level and a first filter slice is stacked with the base filter to modify a beam quality of a radiation beam of a first energy level higher than the base energy level. In a beam filter positioning device, a base stage carries a base filter and a first stage carries a filter slice. The base stage is provided with a first engagement site and a second engagement site. The first stage is provided with a first engagement site, a second engagement site, and an open port. The first stage and the base stage are each independently movable relative to the beamline. The first stage is engageable with the base stage when at least one of the first and second engagement sites of the first stage is aligned with at least one of the first and second engagement sites of the base stage, and is further movable with the base stage in unison when engaged.

24 Claims, 10 Drawing Sheets

BEAM FILTER ASSEMBLY AND BEAM FILTER POSITIONING DEVICE

TECHNICAL FIELD

Embodiments of this disclosure relate generally to radiation apparatuses and methods. In particular, various embodiments of a beam filter assembly and a beam filter positioning device are described.

BACKGROUND

Linear accelerators (LINACs) are used to produce high energy radiation beams useful in radiation therapy and imaging of patients and in other applications such as safety inspection. A linear accelerator includes various devices operable to produce, condition, or monitor radiation beams. By way of example, an x-ray target produces x-rays upon impingement by energetic electrons. A beam filter such as a photon flattening filter conditions x-rays to provide a desired energy or dose distribution profile across the radiation field. In an electron mode operation of a linear accelerator, a scattering foil and button is used to scatter incident electrons to provide a broadened, uniform beam profile.

In conventional linear accelerators, full sized beam filters are used in filtration of x-ray beams of different energy levels. For x-ray beams of high energy levels such as 18 MV, 20 MV or higher, a beam filter may be composed of multiple materials to create a desired filtration. The use of full sized beam filters for radiation beams of different energy levels requires greater filter material volumes and sizes and increases manufacturing costs.

Conventional beam filter positioning devices include exchangers which are designed to carry full sized beam filters and allow switching of individual filters for beams of different energy levels. For example, a conventional carousel exchanger is designed to carry five full sized individual filters for filtration of beams of five different energy levels. This kind of positioning device design requires more space or clearance for full sized filters' movement and more complicated motion axes for positioning and retracting beam filters in and/or out of the beam path.

SUMMARY

The present disclosure uses layers of filter slices and stacks them together to provide desired filtration. For example, a filter assembly may include a base filter and one or more filter slices. Each of the base filter and filter slices can be made of an x-ray attenuating material to remove energy from an x-ray beam. The beam exiting the base filter and filter slice(s) can thus be flattened to its desired energy level. The base filter can be configured to provide flattening for the lowest energy radiation beam output. One or more filter slices can be stacked on top or bottom of the base filter. The combination of the base filter and a stacked filter slice can flatten an x-ray output beam at a higher energy level than the base filter does. Multiple slices can be stacked with the base filter for filtration of an x-ray beam at a higher energy level.

In an embodiment, a beam filter assembly includes a base filter and a first filter slice. The base filter is configured to modify a beam quality of a radiation beam of a base energy level. The first filter slice is stackable with the base filter when in use to modify a beam quality of a radiation beam of a first energy level higher than the base energy level. The base filter and the first filter slice each can be independently moved in and/or out of a beamline by a linear motion axis or a rotary motion axis. The base filter can be configured to modify an energy distribution of the radiation beam of the base energy level, and the first filter slice can be stacked with the base filter to modify an energy distribution of the radiation beam of the first energy level. Alternatively or additionally, the base filter can be configured to modify a dose distribution of the radiation beam of the base energy level, and the first filter slices can be stacked with the base filter to modify a dose distribution of the radiation beam of the first energy level.

In some embodiments, the beam filter assembly may further include a second filter slice stackable with the first filter slice and/or the base filter when in use. The second filter slice can be configured to stack with the first filter slice and the base filter when in use to modify the beam quality of the radiation beam of the second energy level. Alternatively, the second filter slice can be configured to stack with the base filter when in use to modify the beam quality of the radiation beam of the second energy level. The second filter slice can be configured to stack with the first filter slice and/or the base filter to modify an energy distribution and/or a dose distribution of the radiation beam of the second energy level. The base filter, the first and second filter slices each can be independently moved in and/or out of a beamline.

In some embodiments, the beam filter assembly may further include a third filter slice stackable with the second and first filter slices, and/or with the base filter when in use to modify a beam quality of a radiation beam of a third energy level higher than the second energy level. The third filter slice can be configured to stack with the second and first filter slices, and the base filter when in use to modify the beam quality of the radiation beam of the third energy level. Alternatively, the third filter slice can be configured to stack with the base filter when in use to modify the beam quality of the radiation beam of the third energy level. The third filter slice can be configured to stack with the second and first filter slices, and/or the base filter to modify an energy distribution and/or a dose distribution of the radiation beam of the third energy level. The base filter, the first, second and third filter slices can be each independently moved in and/or out of the beamline.

In some embodiments, the beam filter assembly may further include a fourth filter slice stackable with the third, second, and first filter slices, and/or with the base filter to modify a beam quality of a radiation beam of a fourth energy level higher than the third energy level. The fourth filter slice can be configured to stack with the third, second and first filter slices, and the base filter when in use to modify the beam quality of the radiation beam of the fourth energy level. Alternatively, the fourth filter slice can be configured to stack with the base filter when in use to modify the beam quality of the radiation beam of the fourth energy level. The fourth filter slice can be configured to stack with the third, second and first filter slices, and/or the base filter to modify an energy distribution and/or a dose distribution of the radiation beam of the fourth energy level. The base filter, the first, second, third, and fourth filter slices can be each independently moved in and/or out of the beamline.

In a specific embodiment, an exemplary beam filter assembly includes a base filter configured to modify a beam quality of a radiation beam of a base energy level at about 4 MV, a first filter slice configured to stack with the base filter when in use to modify a beam quality of a radiation beam of a first energy level at about 6 MV, a second filter slice configured to stack with the first filter slice and the base filter when in use to modify a beam quality of a radiation beam of a second energy level at about 10 MV, a third filter slice configured to stack with the second and first filter slices and the base filter when in use to modify a beam quality of a radiation beam of a third energy level at about 15 MV, and a fourth filter slice configured to stack with the third, second, and first filter slices and the base filter when in use to modify a beam quality of a radiation beam of a fourth energy level at about 18 MV.

In some embodiments, the disclosure provides a beam filter assembly comprising a base filter configured to modify a beam quality of a radiation beam of a base energy level and N filter slices each being stackable with the base filter (N being an integer of 1-10). The N filter slices are configured such that a $1^{st}$ filter slice is for use at least in modifying a radiation beam of a $1^{st}$ energy level, a $2^{nd}$ filter slice for use at least in modifying a radiation beam of a $2^{nd}$ energy level, and in such successive order that an $(N-1)^{th}$ filter slice is for use at least in modifying a radiation beam of an $(N-1)^{th}$ energy level, and an $N^{th}$ filter slice for use at least in modifying a radiation beam of an $N^{th}$ energy level, and that the $N^{th}$ energy level is higher than the $(N-1)^{th}$ energy level, and in such successive order that the $2^{nd}$ energy level is higher than the $1^{st}$ energy level, and the $1^{st}$ energy level is higher than the base energy level. When an $M^{th}$ filter slice (M being an integer≤N) is stacked with the base filter in use to modify a radiation beam of an $M^{th}$ energy level, the $1^{st}$ through $(M-1)^{th}$ filter slices are stacked between the $M^{th}$ filter slice and the base filter. The base filter and the N filter slices can be each configured to modify an energy spectrum and/or a dose distribution of a radiation beam. The base filter and N filter slices each can be independently moved in and/or out of the beamline by a linear motion axis or a rotary motion axis.

The present disclosure further provides a beam filter positioning device that can index layers of filter slices. An exemplary beam filter positioning device uses tiered linear stages to provide a desired x-ray filter combination. Each stage may carry a filter or filter slice, be provided with an open port, and include engagement sites for engaging with an actuator key. Each stage may be moved to position a filter or filter slice or an open port in the beam path. The position of the stage may be set by an actuator key that engages the stages at one of the engagement sites to create the filter and open port combination. Scattering foils and electron buttons can also be carried by the beam filter positioning device and indexed in a similar fashion.

In an embodiment, a beam filter positioning device includes a base stage carrying a base filter and one or more additional stages each carries a filter slice. The base stage is provided with a first engagement site and a second engagement site. The one or more additional stages include at least a first stage carrying a first filter slice and being provided with a first engagement site, a second engagement site, and an open port. The first stage and the base stage are each independently movable relative to the beamline. The first stage is engageable with the base stage when at least one of the first and second engagement sites of the first stage is aligned with at least one of the first and second engagement sites of the base stage, and further movable with the base stage in unison when engaged.

The first stage and the base stage each can be independently moved by a linear motion axis. When engaged, the first stage and the base stage can be further moved in unison by an additional linear motion axis. Alternatively, the first stage and the base stage each can be independently moved by a rotary motion axis, and when engaged the first stage and the base stage can be further moved in unison.

The first stage and the base stage can be arranged such that when the first engagement site of the first stage is aligned with the first engagement site of the base stage, the first filter slice carried by the first stage is stacked with the base filter carried by the base stage, and the first stage can be engaged and further moved with the base stage in unison to position the stacked first filter slice and base filter in the beamline; or when the second engagement site of the first stage is aligned with the first engagement site of the base stage, the open port provided in the first stage is aligned with the base filter carried by the base stage, and the first stage can be further moved with the base stage in unison to position the open port of the first stage and the base filter carried by the base stage in the beamline.

In some embodiments, the first stage and the base stage each can further carry a scattering foil, and the first stage and the base stage can be arranged such that when the second engagement site of the first stage is aligned with the first engagement site of the base stage, the first stage can be engaged and further moved with the base stage in unison to position the scattering foil carried by the base stage in the beamline; or when the first engagement site of the first stage is aligned with the second engagement site of the base stage, and the first stage can be engaged and further moved with the base stage in unison to position the scattering foil carried by the first stage in the beamline.

In some embodiments, the first stage and the base stage can be provided with apertures at the first and second engagement sites of the first stage and base stage respectively. The beam filter positioning device may further include an actuator key operable to engage each of the apertures at the first and second engagement sites of the first stage and the base stage. The actuator key can be controlled by a control.

In some embodiments, the beam filter positioning device may further include a second stage carrying a second filter slice. The second stage may be provided with a first engagement site, a second engagement site, and an open port, and independently movable relative to the beamline. The second stage is engageable with the first stage when at least one of the first and second engagement sites of the second stage is aligned with at least one of the first and second engagement sites of the first stage, and further movable with the first stage in unison when engaged. The second stage is engageable with the first stage and the base stage when at least one of the first and second engagement sites of the second stage is aligned with at least one of the first and second engagement sites of the first stage and the base stage, and further movable with the first stage and the base stage in unison when engaged. The first stage, the second stage, and the base stage each can be independently moved by a linear motion axis. When engaged the first stage and the second stage can be further moved in unison by an additional linear motion axis. Further, when engaged the first stage, the second stage and the base stage can be further moved in unison.

The first stage, the second stage, and the base stage each can be provided with apertures at the first and second engagement sites of the first stage, the second stage, the base stage respectively, and the beam filter positioning device may further include an actuator key operable to engage each of the apertures at the first and second engagement sites of the first stage, the second stage, and the base stage respectively. The actuator key can be controlled by a control.

The first stage, the second stage, and the base stage can be arranged such that when the first engagement sites of the first and second stages are aligned with the first engagement site of the base stage, the first filter slice carried by the first stage and the second filter slice carried by the second stage are stacked with the base filter carried by the base stage, and the first and second stages can be engaged and further moved with the base stage in unison to position stacked first and second filter slices and base filter in the beamline; or when the first engagement sites of the first and second stages are aligned with the second engagement site of the base stage, the open ports in the first and second stages are aligned with the base filter carried by the base stage, and the first and second stages can be engaged and further moved with the base stage in unison to position the aligned open ports and base filter in the beamline.

The first stage, the second stage, and the base stage each can further carry a scattering foil, and the first stage, the second stage, and the base stage can be arranged such that when the second engagement sites of the first and second stages are aligned with the first engagement site of the base stage, the first and second stages can be engaged and further moved with the base stage in unison to position the scattering foil carried by the base stage in the beamline; or when the first engagement site of the first stage is aligned with the second engagement sites of the second stage and base stage, and the first stage can be engaged and further moved with the second stage and the base stage in unison to position the scattering foil carried by the first stage in the beamline; or when the first engagement site of the second stage is aligned with the second engagement sites of the first stage and base stage, and the second stage can be engaged and further moved with the first stage and the base stage in unison to position the scattering foil carried by the second stage in the beamline.

In some embodiments, the beam filter positioning device can include 1-10 additional stages each carrying a filter slice, provided with an open port, a first engagement site and a second engagement site, and independently movable relative to the beamline. The base stage and each of the 1-10 additional stages may further carry a scattering foil. The base stage and each of 1-10 additional stages each can be independently moved by a linear motion axis. The base stage can be engaged and moved with the 1-10 additional stages in unison by an additional linear motion axis.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Figure 1:
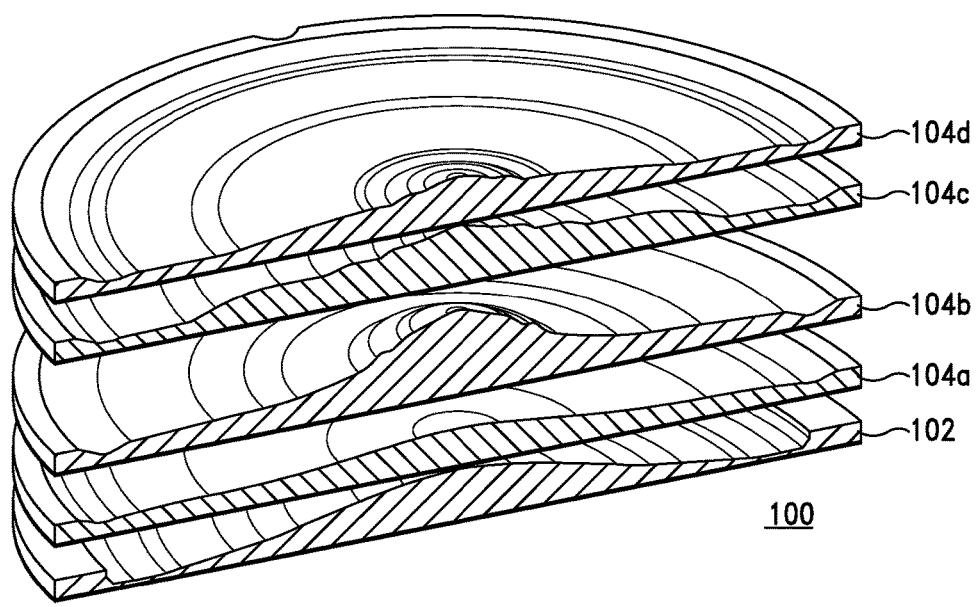
FIG. 1 schematically shows an exemplary beam filter assembly according to embodiments of the disclosure.

Various embodiments of beam filter assemblies and beam filter positioning devices are described. It is to be understood that the disclosure is not limited to the particular embodiments described. An aspect described in conjunction with a particular embodiment is not necessarily limited to that embodiment and can be practiced in any other embodiments.

Various embodiments are described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components or process steps may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. Further, the term "first" or "second" etc. may be used to distinguish one element from another in describing various elements e.g. two or more than two elements. It should be noted the terms "first" and "second" as used herein include references to two or more than two. For example, a beam filter position device may include two or more movable stages each carrying a filter slice. Further, the use of the term "first" or "second" should not be construed as in any particular order unless the context clearly dictates otherwise.

Various relative terms such as "top," "bottom," "above," "under," "upper," and "lower," etc. may be used to facilitate description of various embodiments. The relative terms are defined with respect to a conventional orientation of a structure and do not necessarily represent an actual orientation of the structure in manufacture or use. The following detailed description is, therefore, not to be taken in a limiting sense.

As used herein, the phrase "a radiation beam of an energy level" refers to a beam output of a radiation machine operated at an energy level. By way of example, a radiation beam of an energy level at 4 MV refers to a beam produced by a radiation machine operated at the energy level of 4 MV. Similarly, a radiation beam of an energy level at 18 MV refers to a beam produced by a radiation machine operated at the energy level of 18 MV, and so on.

As used herein, the phrase "a beam quality of a radiation beam" refers to an energy spectrum of a radiation beam, a dose distribution of a radiation beam, or the shape or direction of a radiation beam. A radiation beam includes but is not limited to a beam of x-rays, protons, heavy ions, electrons or the like.

As used herein, the term "beam filter" and "base filter" may be used interchangeably and refer to a component that can be used independently or in combination with one or more filter slices to modify a beam quality of a radiation beam of an energy level useful in clinical applications. By way of example, a beam filter may be designed, engineered or configured to remove the lower energy from a radiation beam, to flatten a dose distribution of a radiation beam, and/or to improve the symmetry of a radiation beam.

As used herein, the term "filter slice" refers to a component that is used in combination with a base filter or with a base filter and other filter slice(s) to collectively modify a beam quality of a radiation beam of an energy level. In general, a filter slice is not used independently or with other filter slices only in clinical applications.

As used herein, the term "scattering foil" refers to a component that is used to broaden the profile of a thin beam of electrons, or protons, etc.

Layering of Filters for Radiation Beam Filtration

FIG. 1 schematically shows an exemplary beam filter assembly 100 according to embodiments of the disclosure. The beam filter assembly 100 includes a base filter 102 and a plurality of filter slices 104a-104d stackable with the base filter 102. Four filter slices are shown in FIG. 1 for illustration purpose. It should be appreciated that fewer or more than four filter slices can be included in the beam filter assembly of the disclosure. For example, the beam filter assembly of the disclosure can include a base filter and a single filter slice. The beam filter assembly may also include a base filter and multiple filter slices e.g. up to 10, 20, 50, or more. In general, the beam filter assembly of the disclosure may include as many filter slices as the number of the energy levels under which a radiation machine operates. Further, in FIG. 1 the filter slices 104a-104d are shown as being stacked on top of the base filter 102. It should be appreciated that the beam filter assembly 100 can be arranged or configured such that the filter slices 104a-104d are stackable under the base filter 102 when in use.

The base filter 102 can be designed to modify the characteristics of a radiation beam of the lowest energy level under which a radiation machine operates. For ease of description, the letter "X" is used herein to refer to the energy level (MV) under which a radiation machine operates. By way of example, the term "4X base filter" refers to a base filter that is configured to modify a beam quality of a radiation beam produced by a radiation machine operated at the energy level of 4 MV. The base filter can be any of 1X to 18X filter.

The base filter 102 can be used independently in clinical or other applications. In various embodiments of the disclosure, the base filter 102 is used in combination with one or more filter slices 104a-104d to modify beam qualities of radiation beams of higher energy levels, as will be described in greater detail below.

The base filter 102 may be configured to modify the energy spectrum, dose distribution, or intensity of a radiation beam, etc. An unfiltered radiation beam produced by a megavoltage radiation machine typically has a sharply peaked distribution with respect to energy, dose rate, or intensity etc. Therefore, beam filters are typically used to condition or modify the characteristics of the beams in order to meet the requirements for clinical applications. By way of example, a beam filter can be designed to selectively remove low energy from the energy spectrum of a beam to provide a "hardened" high energy beam. In another example, a beam filter can be used to flatten the dose distribution curve of a radiation beam by e.g. reducing the dose rate at the beam center. The symmetry of a radiation beam can also be improved by using a beam filter. In general, a beam filter can be made of a partially radiation attenuating material. Suitable materials include but are not limited to copper, aluminum, lead, or the like. Manufacturing of various beam filters is known in the art and its detailed description is therefore omitted herein. In some embodiments, a beam filter can be made of multiple materials to create a desired filtration.

Referring to FIG. 1, the filter slice(s) 104a-104d is (are) stackable with the base filter 102. In use, the filter slice(s) 104a-104d is (are) stacked or combined with the base filter 102 to collectively modify the characteristics of a beam of an energy level higher than that of the beam modified by the base filter 102 alone. FIG. 1 shows an embodiment where multiple filter slices 104a-104d are stacked with the base filter 102 in use. In some embodiments, each of the multiple filter slices 104a-104d can be designed to separately or independently stack with the base filter 102 for modifying a radiation beam of a higher energy level. By way of example, a base filter 102 can be a 4X base filter. A first filter slice 104a can be designed to stack with the base filter 102 and the stacked first filter slice 104a/base filter 102 modifies a radiation beam of an energy level at 6 MV when in use. In another example, a second filter slice 104b can be designed to stack with the base filter 102 and the stacked second filter slice 104b/base filter 102 modifies a radiation beam of an energy level at 10 MV when in use. In a further example, a third filter slice 104c can be designed to stack with the base filter 102 and the stacked third filter slice 104c/base filter 102 modifies a radiation beam of an energy level at 15 MV when in use. In a further example, a fourth filter slice 104d is designed to stack with the base filter 102 and the stacked fourth filter slice 104d/base filter 102 modifies a radiation beam of an energy level at 18 MV when in use, and so on.

The above examples are provided for illustration purpose. It should be appreciated that the base filter 102 can be designed to modify a radiation beam of an energy level lower or greater than 4 MV. For example, the base filter 102 can be a 1X filter, 2X filter, 3X filter, 5X filter, or 6X filter, etc., and each of the filter slices 104a-104d can be configured such that the stacked base filter and one of the filter slices 104a-104d can modify a beam quality of a radiation beam of a higher energy level.

The base filter 102 and filter slice(s) 104a-104d can be stacked using movable stages, as will be described in greater detailed below. Each of the movable stages can be driven by a motion axis such as a linear or rotary motion axis to allow stacking and positioning of the stacked filter slice/base filter in and/or out of the beam path. Feedback sensors can be used to confirm alignment or positions of the base filter 102 and filter slices 104a-104d. Feedback sensors can be provided on the filter and/or filter slices, movable stages, or any other suitable locations providing signals capable of determining positions of the filter and/or filter slices. In some embodiments, an ion chamber can be used as a secondary check for beam quality to confirm the beam profile, flatness, or symmetry, etc.

In various embodiments of the disclosure, a plurality of filter slices can be stacked with a base filter when in use, as shown in FIG. 1. In such embodiments, filter slices are designed such that they can be shared between energy levels when in use. Combinations of filter slices can be arranged according to the energy levels of radiation beams to be modified, as will be described in greater detail below in connection with FIGS. 2A-2E.

FIGS. 2A through 2E illustrate various combinations or arrangements of filter slices with a base filter of a beam filter assembly according to embodiments of the disclosure. The beam filter assembly 200 includes a base filter 202, a first filter slice 204a, a second filter slice 204b, a third filter slice 204c, and a fourth filter slice 204d. It should be noted that the principle described herein can be applied to a beam filter assembly that includes fewer or more than four filter slices.

Figure 2A:
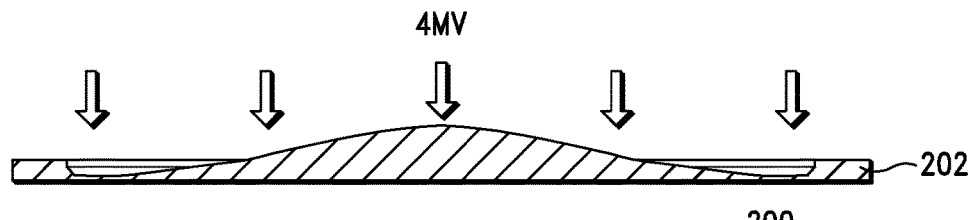
FIGS. 2A through 2E schematically show various combinations of filter slices with a base filter of an exemplary beam filter assembly according to embodiments of the disclosure.

FIG. 2A shows a base filter 202 (e.g. 4X base filter) positioned in a radiation beam. In this arrangement of the beam filter assembly 200, the base filter 102 is used alone or independently in modifying a radiation beam of a base energy level at 4 MV. In this arrangement, the first through fourth filter slices 204a-204d (not shown in FIG. 2A) are retracted from the beam path such that they are not stacked with the base filter 202.

Figure 2B:
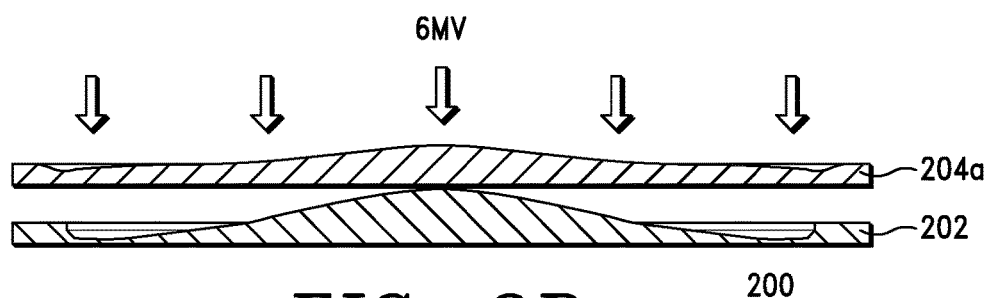

FIG. 2B shows an arrangement of the beam filter assembly 200 where the 4X base filter 202 and the first filter slice 204a are stacked and positioned in a beam path. The first filter slice 204a can be designed such that the combination of the first filter slice 204a and the base filter 202 modifies a radiation beam of an energy level at e.g. 6 MV. For purpose of description, the first filter slice 204a is hereafter referred to as (6X-4X) delta slice. In this arrangement, the second through fourth filter slices 204b-204d (not shown in FIG. 2B) are retracted from the beam path such that they are not stacked with the base filter 202 and the first filter slice 204a. The arrangements illustrated in FIGS. 2A and 2B show that the base filter (4X) of the beam filter assembly 200 can be used or shared in modifying radiation beams of energy levels at both 4 MV and 6 MV.

Figure 2C:
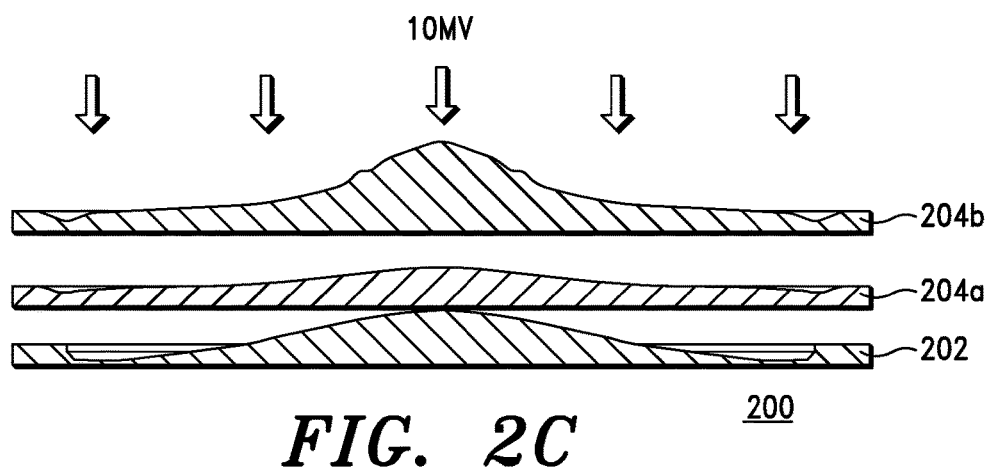

FIG. 2C shows an arrangement of the beam filter assembly 200 where the 4X base filter 202, the first filter slice 204a ((6X-4X) delta slice), and the second filter slice 204b are stacked and positioned in a beam path. The second filter slice 204b can be designed such that its combination with the first filter slice 204a ((6X-4X) delta slice) and the 4X base filter 202 modifies a radiation beam of an energy level e.g. at 10 MV. For purpose of description, the second filter slice 204b is hereafter referred to as (10X-6X) delta slice. In this arrangement, the third and fourth filter slices 204c-204d (not shown in FIG. 2C) are retracted such that they are not stacked with the second filter slice 204b, the first filter slice 204a, and the base filter 202. The arrangements illustrated in FIGS. 2A, 2B and 2C show that the base filter (4X) of the beam filter assembly 200 can be used or shared in modifying radiation beams of energy levels at all of 4 MV, 6 MV, and 10 MV. The first filter slice 204a, or (6X-4X) delta slice, of the beam filter assembly 200 can be used or shared in modifying radiation beams of energy levels at both 6 MV and 10 MV.

Figure 2D:
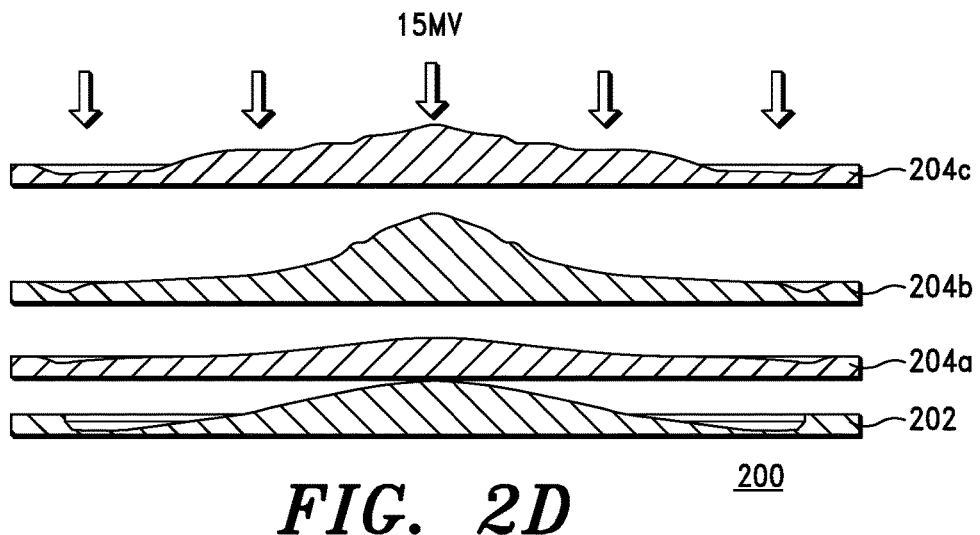

FIG. 2D shows an arrangement of the beam filter assembly 200 where the 4X base filter 202, the first filter slice 204a ((6X-4X) delta slice), the second filter slice 204b ((10X-6X) delta slice), and the third filter slice 204c are stacked and positioned in a beam path. The third filter slice 204c can be designed such that its combination with the second filter slice 204b ((10X-6X) delta slice), the first filter slice 204a ((6X-4X) delta slice), and the 4X base filter 202 modifies a radiation beam of an energy level e.g. at 15 MV. For purpose of description, the third filter slice 204c is referred to as (15X-10X) delta slice. In this arrangement, the fourth filter slice 204d (not shown in FIG. 2D) is retracted such that it is not stacked with the first through third filter slices 204a-204c and the base filter 202. The arrangements illustrated in FIGS. 2A, 2B, 2C, and 2D show that the base filter (4X) of the beam filter assembly 200 can be used or shared in modifying radiation beams of energy levels at all of 4 MV, 6 MV, 10 MV, and 15 MV. The first filter slice 204a, or (6X-4X) delta slice of the beam filter assembly 200, can be used or shared in modifying radiation beams of energy levels at all of 6 MV, 10 MV, and 15 MV. The second filter slice 204b, or (10X-6X) delta slice, can be used or shared in modifying radiation beams of energy levels at both 10 MV and 15 MV.

Figure 2E:
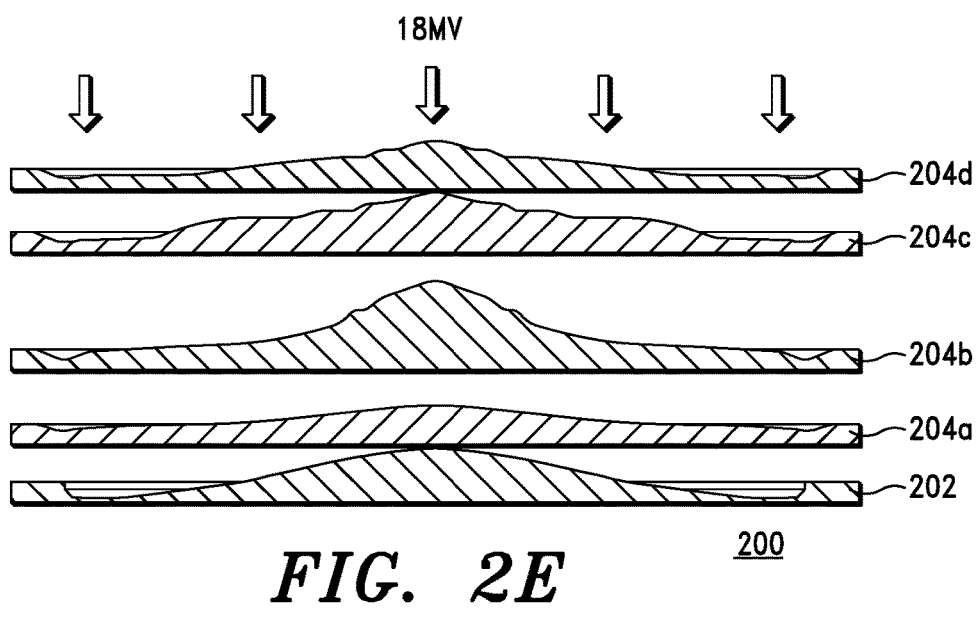

FIG. 2E shows an arrangement of the beam filter assembly 200 where the 4X base filter 202, the first filter slice 204a ((6X-4X) delta slice), the second filter slice 204b ((10X-6X) delta slice), the third filter slice 204c ((15X-10X) delta slice), and the fourth filter slice 204d are stacked and positioned in a beam path. The fourth filter slice 204d can be designed such that its combination with the third, second, and first filter slices 204a-204c and the base filter 202 modifies a radiation beam of an energy level e.g. at 18 MV. For purpose of description, the fourth filter slice 204d is hereafter referred to as (18X-15X) delta slice. The arrangements illustrated in FIGS. 2A, 2B, 2C, 2D, and 2E show that the base filter (4X) of the beam filter assembly 200 can be used or shared in modifying radiation beams of energy levels at all of 4 MV, 6 MV, 10 MV, 15 MV, and 18 MV. The first filter slice 204a, or (6X-4X) delta slice, can be used or shared in modifying radiation beams of energy levels at all of 6 MV, 10 MV, 15 MV and 18 MV. The second filter slice 204b, or (10X-6X) delta slice, can be used or shared in modifying radiation beams of energy levels at all of 10 MV, 15 MV, and 18 MV. The third filter slice 204c, or (18X-10X) delta slice, can be used or shared in modifying radiation beams of energy levels at both 15 MV and 18 MV.

In conventional linear accelerators, full sized filters are used in filtration of radiation beams of different energy levels. For example, to modify radiation beams of five different energy levels at 4 MV, 6 MV, 10 MV, 15 MV and 18 MV respectively, five different individual beam filters are used, each being a full sized filter and used independently. This conventional design requires a greater total amount of attenuation, a greater material volume and size, thus increases the manufacturing costs. Further, a device for exchanging and storing full sized beam filters requires more clearance and takes up more space inside the radiation machine. Motion axes for positioning beam filters in and/or out of the beam path are also more complicated. One of the advantages of the beam filter assembly of this disclosure is layering of beam filters by using filter slices which can be stacked with a base filter to provide various combinations for filtration of radiation beams of different energy levels. Filter slices can be used or shared between different energy levels. As a result, the total amount of attenuation, volume, and size of the beam filter assembly can be reduced, leading to significant reduction of manufacturing costs. The motion axes for positioning and retracting filter slices can also be simplified, as will be described in greater detail below.

Indexing of Layered Beam Filters

Figure 3:
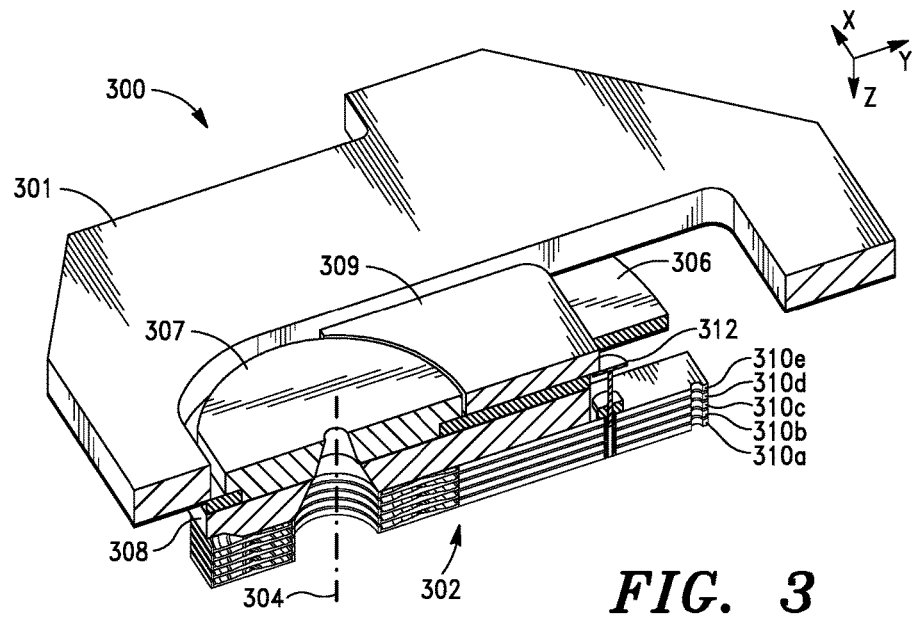
FIG. 3 is a cutaway view of an exemplary radiation apparatus including a beam filter positioning device according to embodiments of the disclosure.

FIG. 3 schematically shows a radiation apparatus 300 according to embodiments of the disclosure. FIG. 3 is a cut-away view showing components of the radiation apparatus 300 in cross-sections. In general, the radiation apparatus 300 includes a source (not shown) and a beam filter positioning device 302 supported by a frame structure 301. The source is operable to produce a radiation beam. The beam filter positioning device 302 operates to position a beam filter and/or other components relative to the source. The source may be a source of electrons or a source of x-rays which may be generated upon impingement of a target by electrons. The source may also be a source of protons or heavy ions. The beam of electrons or x-rays has a central beam path or beamline indicated at 304. The beamline 304 is typically fixed relative to the frame structure 301. The beam filter positioning device 302 is movable relative to the frame structure 301, e.g. in y-direction as shown, to position a beam filter or other components in and/or out of the beamline 304.

The beam filter positioning device 302 may include a movable stage 306 (hereafter "Y-stage"). The movable Y-stage 306 allows components or devices supported thereby to move along y-direction, towards or away from the beamline 304. For example, the Y-stage may support, move and position a collimator 307 in the beamline 304 to generally define the size and shape of the x-ray field, or move the collimator 307 away from the beamline 304 to allow other components such as a scattering foil in the path of electron beams. Shielding 308, 309 disposed adjacent to the collimator 307 may also mount to the Y-stage 306. In various embodiments of the disclosure, the Y-stage 306 may carry a plurality of plates or stages 310a-310e, which may respectively carry a base filter or filter slice, as will be described in greater detail below. The Y-stage 306 may be driven by a motion axis (not shown) secured to the frame structure 301.

Still referring to FIG. 3, the beam filter positioning device 302 may include an actuator key 312 operable to engage the stages 310a-310e. The actuator key 312 may be actuated either by a linear axis or by a rotary axis (not shown) to allow a shaft to protrude into or pull out of engagement apertures in the stages 310a-310e, as will be described in greater detailed below. The actuator key 312 may mount to the Y-stage 306, allowing the engaged stages to further move in unison with the Y-stage 306.

Figure 4:
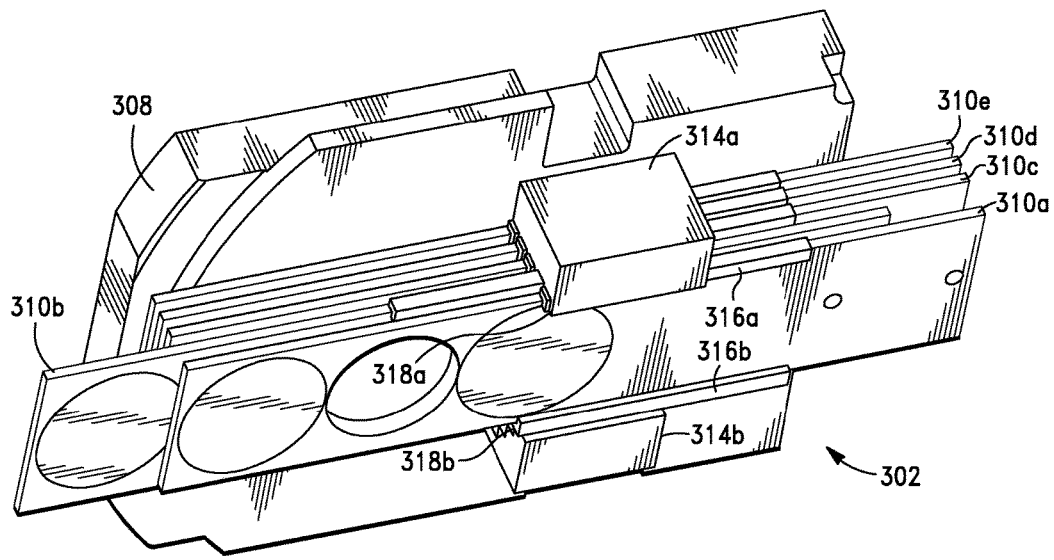
FIG. 4 is an iso bottom view of a beam filter positioning device according to embodiments of the disclosure.

FIG. 4 is an iso bottom view of a beam filter positioning device 302 according to embodiments of the disclosure. As shown, the beam filter positioning device 302 includes a plurality of stages 310a-310e, which may be supported by blocks 314a, 314b. Each of the stages 310a-310e is independently movable relative to the blocks 314a, 314b, e.g., driven by a linear motion axis (not shown). By way of example, each of the stages 310a-310e, e.g. 310a may be provided with slide member e.g. 316a, 316b on either side of the stage, allowing the stage to move along corresponding guide rail members e.g. 318a, 318b provided in the blocks 314a, 314b. The guide rail members 318a, 318b in the blocks 314a, 314b allow the stage 310a to move in the longitudinal direction and hold the stage in the lateral and elevational directions. Any mechanisms that allow each of the stages 310a-310e to independently move may be used. In alternative embodiments, each of the plurality of stages 310a-310e may be moved by a rotary motion axis. The blocks 314a, 314b may mount to and move with the Y-stage 306. Therefore, in addition to the independent movement relative to the blocks 314a, 314b, the stages 310a-310e may further move with the Y-stage 306.

For purpose of description, the bottom stage 310a shown in FIG. 4 may be hereafter referred to as a base stage which may carry a base filter. The other stages tiered above the bottom stage 310a may be referred to as slice stages 310b-310e, each of which may carry a filter slice. It should be noted that alternatively the top stage may be used to carry a base filter and the other stages tiered below the top stage may be used to carry filter slices. Further, while five stages are shown in FIG. 4, fewer or more than five stages may alternatively be used. For example, the beam filter positioning device 302 may include a base stage and one slice stage. Alternatively, the beam filter positioning device 302 may include a base stage and up to 10 or more slice stages to provide various combinations of filter layering. The present disclosure is not limited to the number of the individual stages.

Figure 5A:
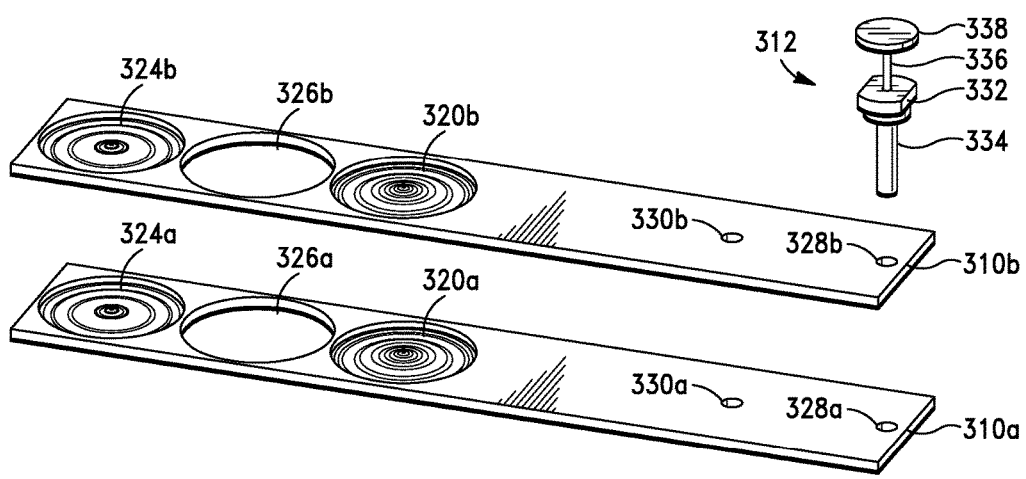
FIGS. 5A and 5B schematically show two movable stages each carrying a beam filter or filter slice and a scattering foil according to embodiments of the disclosure.
Figure 5B:
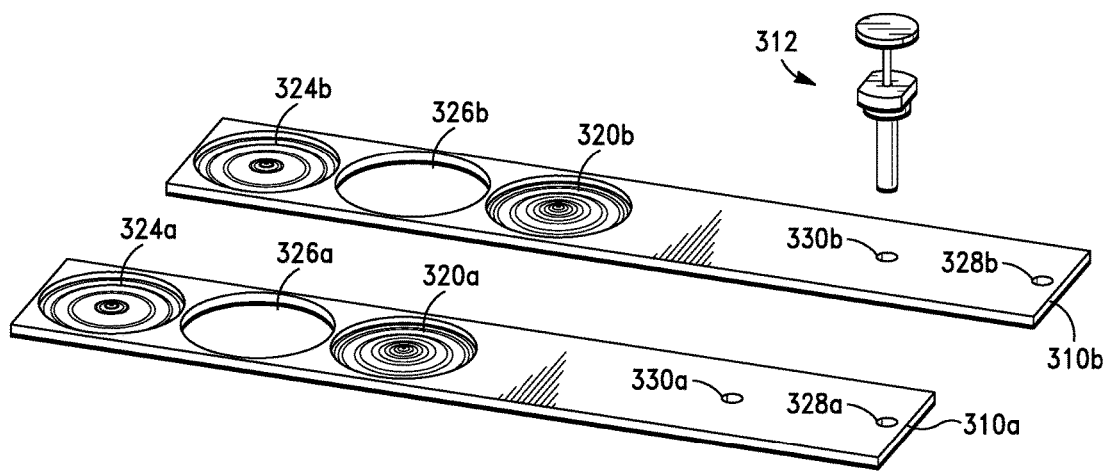

FIGS. 5A and 5B schematically show an exemplary base stage 310a and an exemplary slice stage 310b. In FIGS. 5A-5B, the base stage 310a and slice stage 310b are shown spaced apart in order to illustrate features of the stages and components carried by the stages with greater clarity. In a beam filter positioning device, the stages 310a, 310b can be arranged closely next to each other. As shown, the base stage 310a carries a base filter 320a. The slice stage 310b carries a filter slice 320b. Additionally or alternatively, the base stage 310a may carry a scattering foil 324a and be provided with an open port 326a, the slice stage 310b may carry a scattering foil 324b and be provided with an open port 326b. The base stage 310a has a first engagement site 328a and a second engagement site 330a. The slice stage 310b has a first engagement site 328b and a second engagement site 330b. At the first and second engagement sites 328a, 330a of the base stage 310a, apertures may be provided for receiving the actuator key 312. At the first and second engagement sites 328b, 330b of the slice stage 310b, apertures may be provided for receiving the actuator key 312. While not shown in FIGS. 5A-5B, reference 328c-328e may be used hereafter to describe the first engagements sites in the slice stages 310c-310e respectively, and reference 330c-330e may be used hereafter to describe the second engagements sites in the slice stages 310c-310e respectively. Apertures may be provided at each of the first engagements sites 328c-328e and second engagement sites 310c-310e for receiving the actuator key 312.

Referring to FIG. 5A, the base stage 310a and/or the slice stage 310b may be positioned such that the first engagement site 328a of the base stage 310a is aligned with the first engagement site 328b of the slice stage 310b. The alignment shown in FIG. 5A allows the filter slice 320b on the slice stage 310b to stack with the base filter 320a on the base stage 310a. The actuator key 312 may be actuated to engage the slice stage 310b and base stage 310a at the first engagement sites 328a, 328b. The engaged slice stage 310b/base stage 310a may be then moved in unison to position the stacked filter slice 320b/base filter 320a in a beam path. FIG. 5A shows an exemplary actuator key 312, including a body 332 and an elongate shaft 334 supported by the body 332. A plunger structure 336, which may be driven either linearly or rotationally, moves the body 332 and shaft 334 up and down, causing the shaft 334 to protrude into or pull out of the apertures at the first engagement sites 328a, 328b, engaging the slice stage 310b with the base stage 310a, or disengaging the slice stage 310b from the base stage 310a. The actuator key 312 may mount to the Y-stage 306 e.g. via a handle 338, allowing the engaged base stage 310a and slice stage 310b to move in unison toward or away from the beam path.

Referring to FIG. 5B, the base stage 310a and/or the slice stage 310b may be positioned such that the second engagement site 330b of the slice stage 310b is aligned with the first engagement site 328a of the base stage 310a. The alignment shown in FIG. 5B allows the filter slice 320b to stagger with base filter 320a. In other words, the alignment of the second engagement site 330b of the slice stage 310b with the first engagement site 328a of the base stage 310a allows the base filter 320a on the base stage 310a to be exposed under the open port 326b in the slice stage 310b. The actuator key 312 may be actuated to engage the slice stage 310b and base stage 310a, by causing the shaft 334 to protrude into the apertures at the second engagement site 330b of the slice stage 310b and the first engagement site 328a of the base stage 310a. The engaged base stage 310a and slice stage 310b can be then moved in unison to position the base filter 320a under the open port 326b in a beam path, or the scattering foil 324a in a beam path.

The first engagement sites 328a-328e and the second engagement sites 330a-330e on the base stage 310a and slice stages 310b-310e provides a means for indexing the base filter 320a, slice filters 320b-320e, scattering foils 324a-324e, and open ports 326a-326e. The actuator key 312 operates to engage properly aligned stages, allowing selected filter, filter slice(s) or scattering foil in a beam path, as will be described in greater detail in the following Examples.

Examples

FIGS. 6A-6B through 9A-9C illustrate various operation modes of the radiation apparatus 300 described above in connection with FIGS. 3-5. For purpose of illustration, the base stage 310a is shown to carry a base filter (4X base filter) and a base scattering foil. The first slice stage 310b carries a first filter slice (6X-4X delta slice) and a first scattering foil. The second slice stage 310c carries a second filter slice (10X-6X delta slice) and a second scattering foil. The third slice stage 310d carries a third filter slice (15X-10X delta slice) and a third scattering foil. The fourth slice stage 310e carries a fourth filter slice (18X-15X delta slice) and a fourth scattering foil, and so on. It should be noted that some details such as specific base filter and filter slices for operation at particular energy levels are set forth in order to provide a thorough understanding of the disclosure. It is apparent to one of ordinary skill in the art that these specific details may not be employed or required to practice embodiments of the disclosure.

Figure 6A:
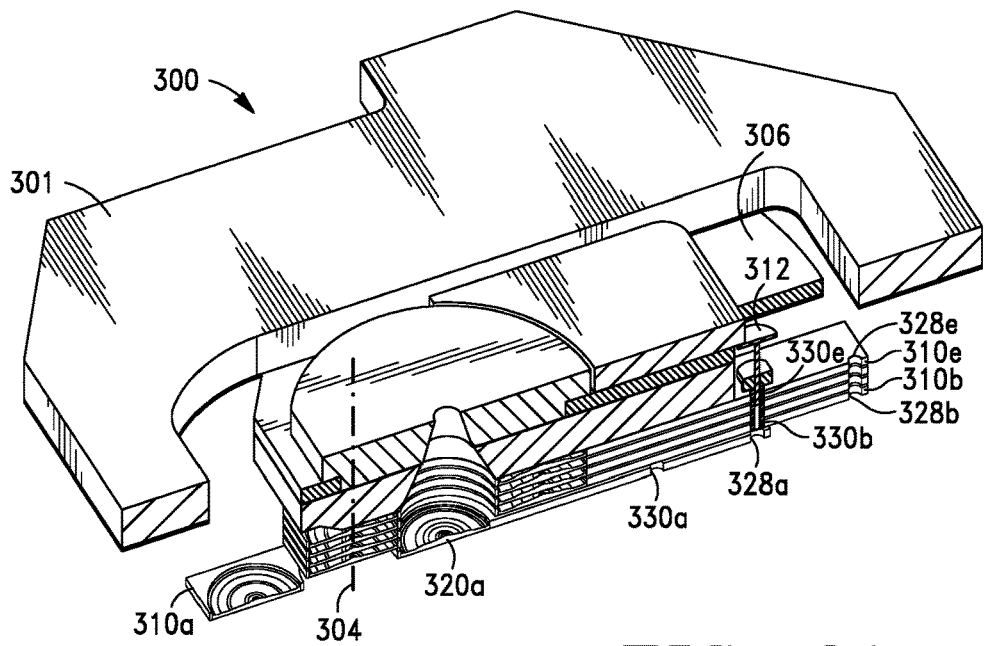
FIGS. 6A and 6B schematically show positioning of a base filter in the beamline of a radiation apparatus according to embodiments of the disclosure.
Figure 6B:
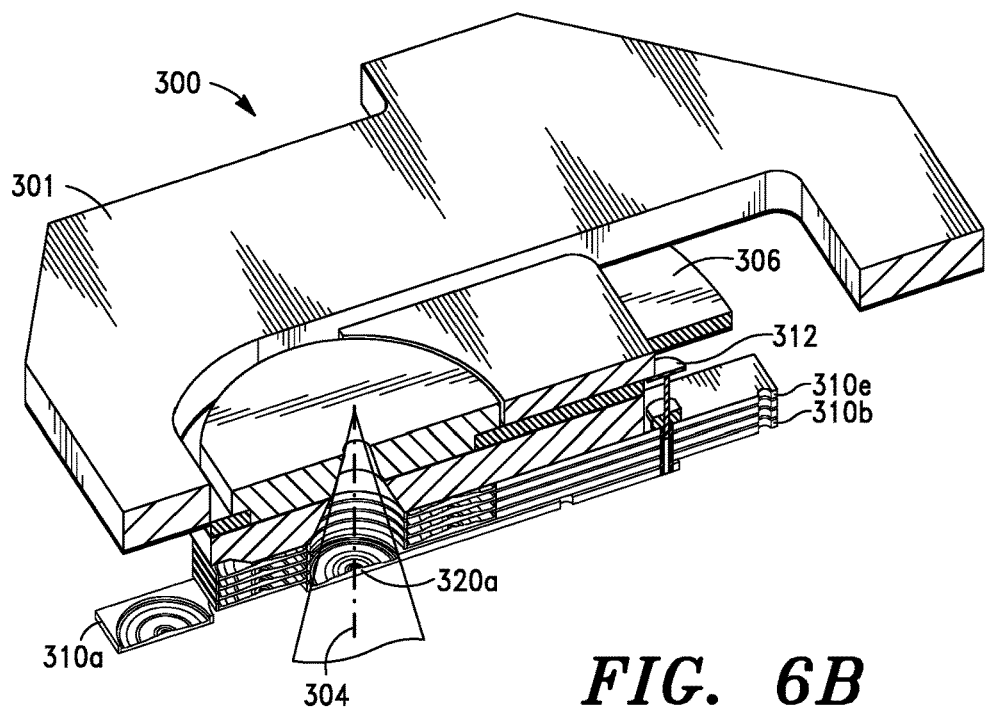

FIG. 6A-6B illustrate an operation mode of the radiation apparatus 300, in which the base filter 320a (4X) is selected and positioned in the beam path 304 for modifying a radiation beam of 4 MV. From a position shown in FIG. 3, the actuator key 312 disengages the base stage 310a at the second engagement site 330a but still engages the first through fourth slice stages 310b-310e at their second engagement sites 330b-330e. The engaged first through fourth slice stages 310b-310e move in unison with Y-stage 306 away from the beamline 304 to a location where the second engagement sites 330b-330e of the first through fourth slice stages 310b-310e align with the first engagement site 328a of the base stage 310a, as shown in FIG. 6A. As shown in FIG. 6A, the base filter 320 on the base stage 310a is now aligned with the open ports in the first through fourth slice stages 310b-310e. The actuator key 312 is actuated to extend further to engage the base stage 310a at the first engagement site 328a. The engaged based stage 310a and first through fourth slice stages 310b-310e can be then moved in unison with the Y-stage 306, towards the beamline 304, positioning or exposing the base filter 320a in the beamline 304, as shown in FIG. 6B. A radiation beam of an energy level at 4 MV can be then generated and conditioned by the 4X base filter.

Figure 7A:
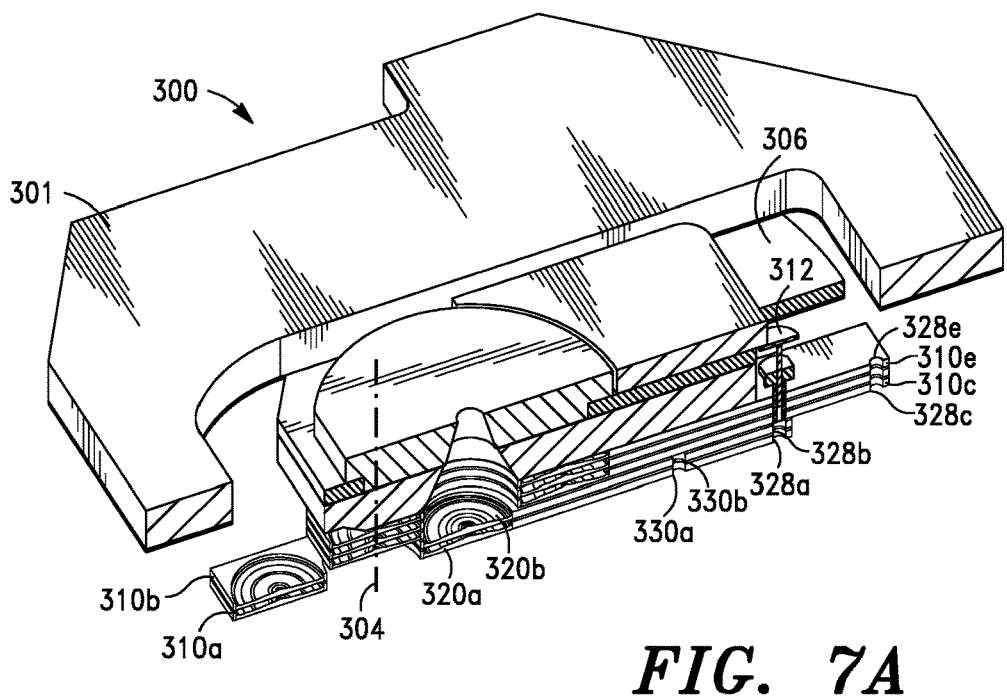
FIGS. 7A and 7B schematically show stacking and positioning of a base filter and a filter slice in the beamline of a radiation apparatus according to embodiments of the disclosure.
Figure 7B:
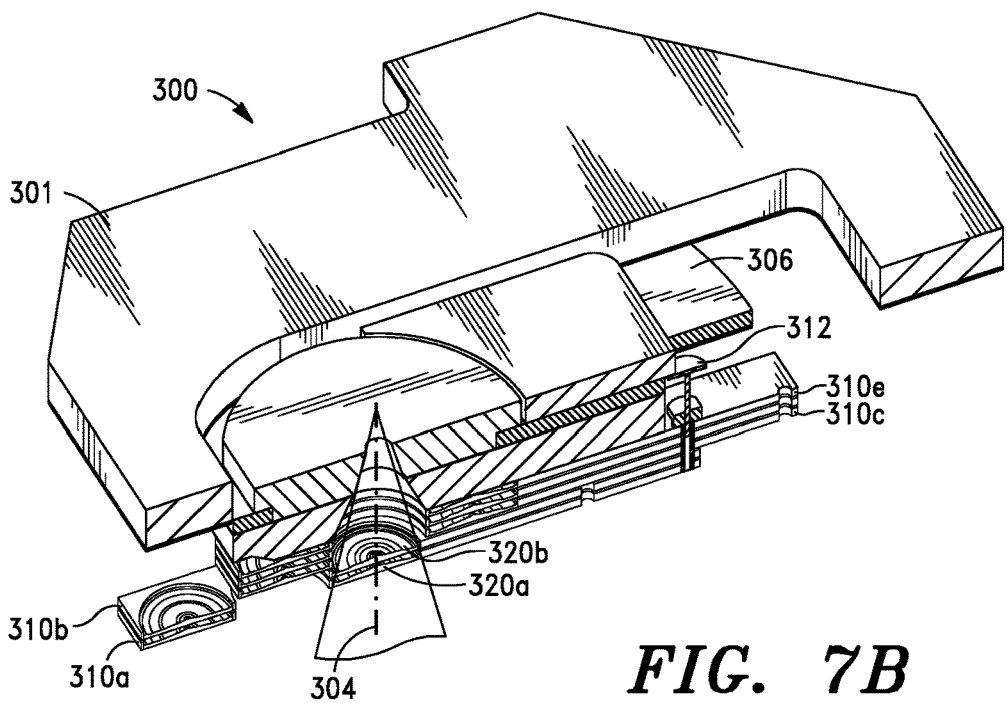

FIGS. 7A-7B illustrate stacking of the first filter slice 320b (6X-4X delta slice) with the base filter 320a (4X) and positioning of the stacked first filter slice 320b and base filter 320a in the beamline 304 for modifying a radiation beam of an energy level at 6 MV. From a position shown in FIG. 3, the actuator key 312 disengages the base stage 310a and the first slice stage 310b at their second engagement sites 330a, 330b but still engages the second through fourth slice stages 310c-310e at their second engagement sites 330c-330e. The engaged second through fourth slice stages 310c-310e move in unison with Y-stage 306 away from the beamline 304 to a location where the second engagement sites 330c-330e of the second through fourth stages 310c-310e align with the first engagement sites 328a, 328b of the base stage 310a and first slice stage 310b as shown in FIG. 7A. As shown in FIG. 7A, the base filter 320a and the first filter slice 320b are now stacked and aligned with the open ports in the second through fourth slice stages 310c-310e. The actuator key 312 can be actuated to extend further in the apertures at the first engagement sites 330a, 330b of the base stage 310a and the first slice stage 310b. The engaged base stage 310a and first through fourth slice stages 310b-310e can be then moved in unison with the Y-stage 306, towards the beamline 304, positioning or exposing the stacked first filter slice 320b and the base filter 320a in the beamline 304, as shown in FIG. 7B. A radiation beam of an energy level at 6 MV can be then generated and conditioned by the stacked 6X-4X delta slice and 4X base filter.

Using the indexing and engagement methods similar to the above shown in FIGS. 7A-7B, the base filter 320a can be stacked with the first and second filter slices 320b, 320c, and the stacked base filter 320a and first and second slices 320b, 320c can be exposed in the beam path to condition a radiation beam of an energy level at 10 MV. In the similar fashion, the base filter 320a can be stacked with the first through third filter slices 320b-320d and the stacked base filter 320a and first through third slices 320b-320d can be exposed in the beam path to condition a radiation beam of an energy level at 15 MV. Similarly, the base filter 320a can be stacked with the first through fourth filter slices 320b-320e and the stacked base filter 320a and first through fourth slices 320b-320e can be exposed in the beam path to condition a radiation beam of an energy level at 18 MV, and so on.

Figure 8A:
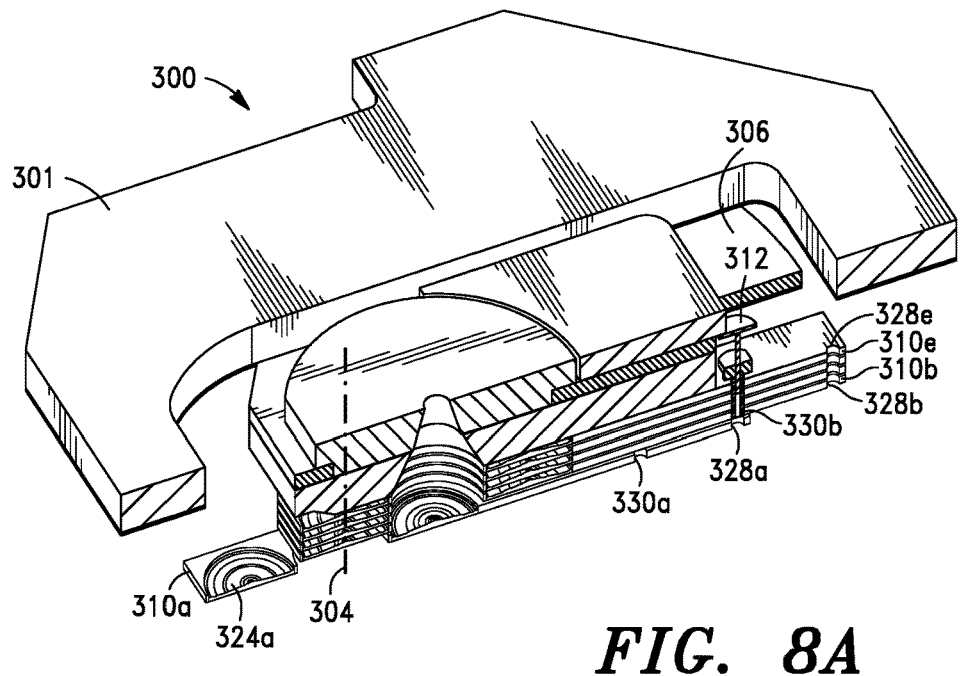
FIGS. 8A and 8B schematically show positioning of a scattering foil in the beamline of a radiation apparatus according to embodiments of the disclosure.
Figure 8B:
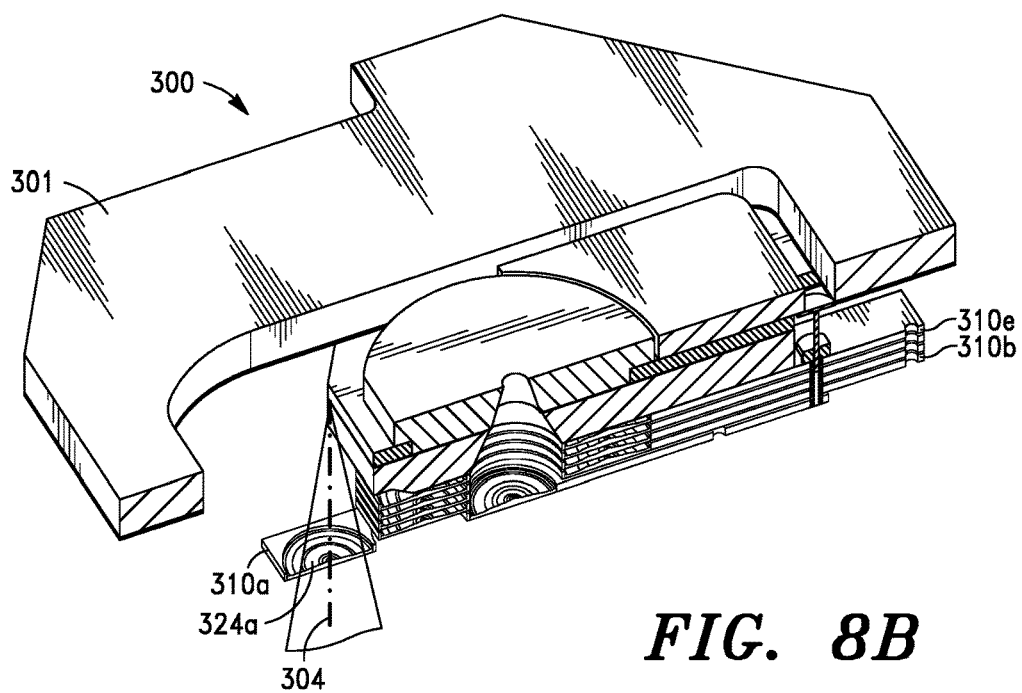

FIGS. 8A and 8B illustrate an operation mode of the radiation apparatus 300, in which a scattering foil 324a carried by the base stage 310a is selected and positioned in the beamline 304 to condition an electron beam of a base energy level. From a position shown in FIG. 3, the actuator key 312 disengages the base stage 310a at the second engagement site 330a but still engages the first through fourth slice stages 310b-310e at their second engagement sites 330b-330e. The engaged first through fourth slice stages 310b-310e move in unison with Y-stage 306 away from the beamline 304 to a location where the second engagement sites 330b-330e of the first through fourth slice stages 310b-310e align with the first engagement site 328a of the base stage 310a as shown in FIG. 8A. A shown in FIG. 8A, the scattering foil 324a staggers from the other scattering foils on the slice stages 310b-310e. The actuator key 312 is actuated to extend further to engage the base stage 310a at the first engagement site 328a. The engaged based stage 310a and first through fourth slice stages 310b-310e can be then moved in unison with the Y-stage 306, further away from the beamline 304, positioning the scattering foils 324a on the base stage 310a in the beamline 304, as shown in FIG. 8B. An electron beam of a base energy level can then be produced and scattered by the scattering foil 324a.

Figure 9A:
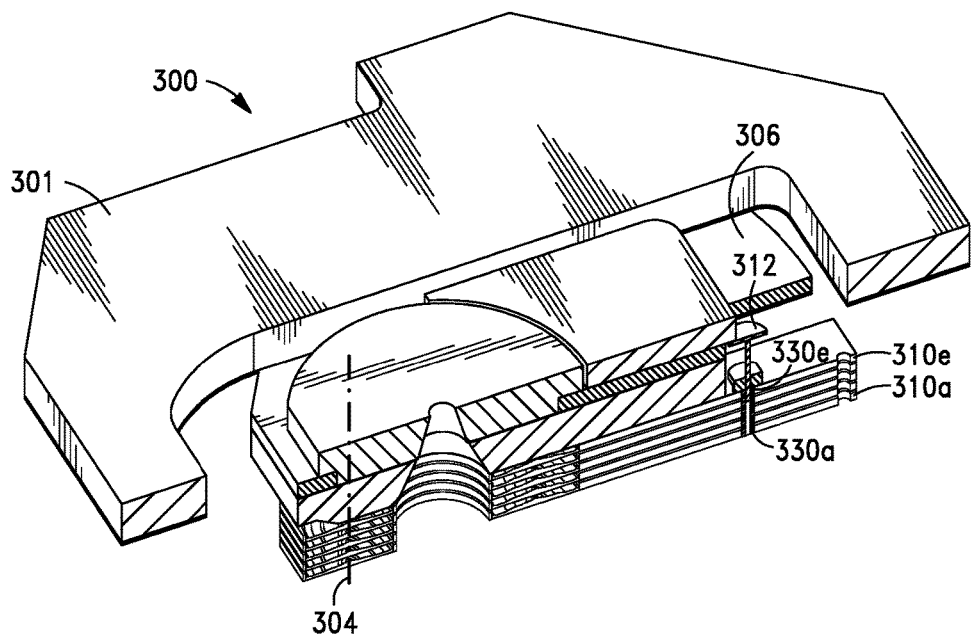
FIGS. 9A through 9D schematically show positioning of another scattering foil in the beamline of a radiation apparatus according to embodiments of the disclosure.
Figure 9B:
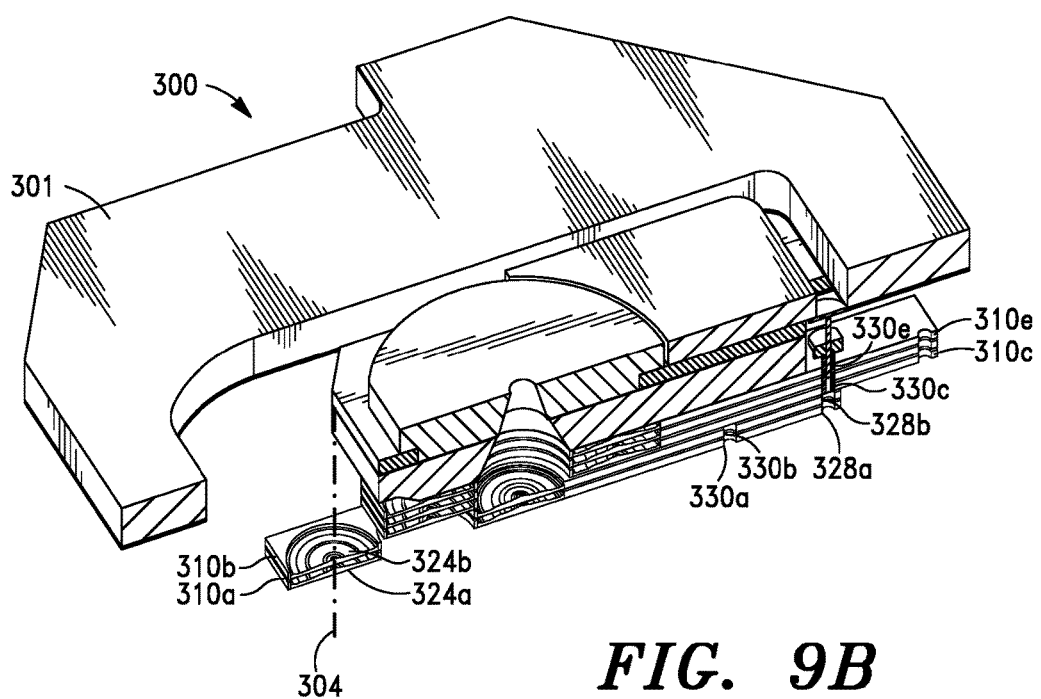
Figure 9C:
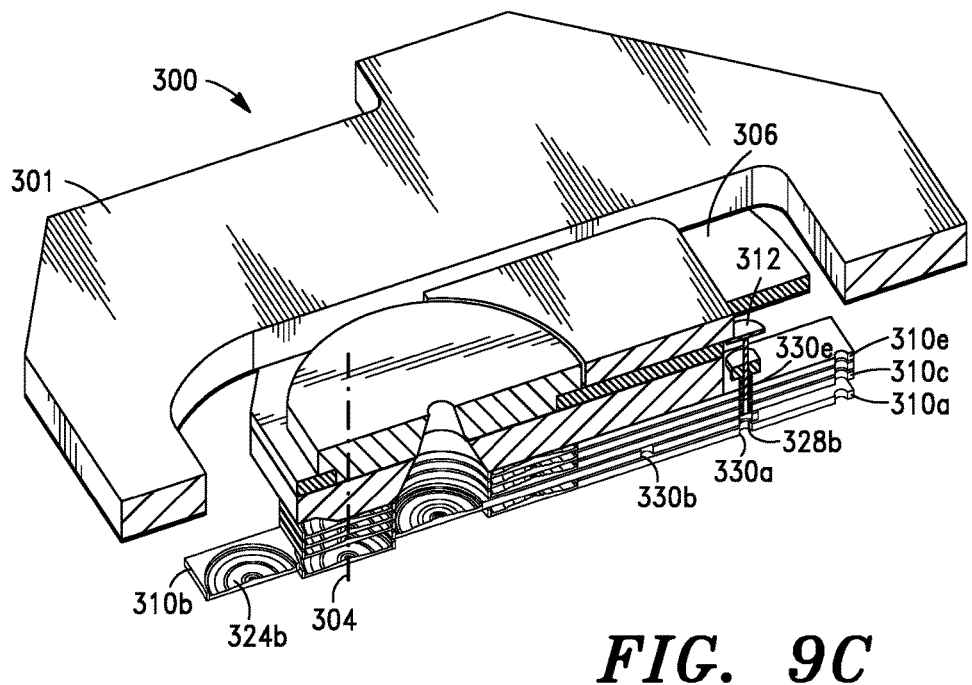
Figure 9D:
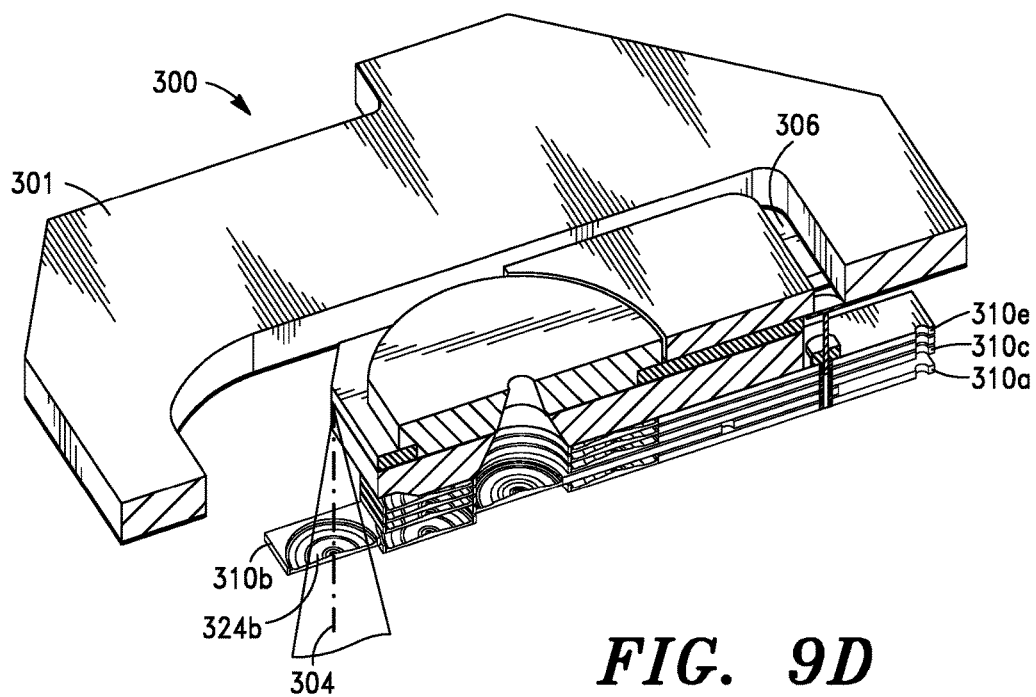

FIGS. 9A through 9D illustrate an operation mode of the radiation apparatus 300, in which the scattering foil 324b carried by the first slice stage 310b is selected and positioned in the beam path to condition an electron beam of a first energy level. From a position shown in FIG. 3, the actuator key 312 engages the base stage 310a and the first through fourth slice stages 310b-310e at the second engagement sites 330a-330e. The engaged base stage 310a and first through fourth slice stages 310b-310e move in unison with the Y-stage 306, away from the beamline 304 as shown in FIG. 9A. The actuator key 312 is then actuated to disengage the base stage 310a and first slice stage 310b but still engage with the second through fourth slice stages 310c-310e. The engaged second through fourth slice stages 310c-310e can be then moved in unison, further away from the beamline 304, to a location wherein the second engagements sites 330c-330e of the second through fourth slice stages 310c-310e align with the first engagement sites 328a-328b of the base stage 310a and the first slice stage 310b, as shown in FIG. 9B. At this location, the scattering foil 324a on the base stage 310a and first scattering foil 324b on the first slice stage 310a are aligned but stagger from other scattering foils on the second through fourth slice stages 310c-310e, as shown in FIG. 9B. Then, the base stage 310a can be individually moved away from the beamline 304 to align the second engagement site 330a with the second engagement sites 330c-330e of the second through fourth slice stages 310c-310e and with the first engagement site 328b of the first slice stage 310b, as shown in FIG. 9C. The actuator key 314 is then actuated to further engage the first engagement site 328b of the first slice stage 310b and the second engagement site 330a of the base stage 310a. The engaged first through fourth slice stages 310b-310e and the base stage 310a can be then moved in unison with the Y-stage 306, further away from the beamline 304, to position the first scattering foil 324b carried by the first slice stage 310b in the beamline 304, as shown in FIG. 9D. An electron beam of a first energy level can then be produced and scattered by the first scattering foil 324b.

Using the similar fashion discussed above in connection with FIGS. 9A-9E, the scattering foils on the second, third or fourth slice stages 310b-310e can be positioned in the beamline 304 respectively, to condition electron beams of different energy levels.

Beam filter assemblies and beam filter positioning devices are described. Those skilled in the art will appreciate that various other modifications may be made within the spirit and scope of the invention. All these or other variations and modifications are contemplated by the inventors and within the scope of the invention.

What is claimed is:

1. A beam filter assembly for use in a radiation machine capable of operating at various energy levels, the beam filter assembly comprising:
   a base filter configured to modify a beam quality of an x-ray beam produced when the radiation machine operates at a base energy level; and
   a first filter slice, wherein the first filter slice is stackable with the base filter and is configured to be used in a combination including the base filter to modify a beam quality of an x-ray beam produced when the radiation machine operates at a first energy level higher than the base energy level,
   wherein the first filter slice is independently movable in and out of a beam line.

2. The beam filter assembly of claim 1, wherein the base filter and the first filter slice are each independently movable in and/or out of a beam line by a linear motion axis.

3. The beam filter assembly of claim 1, wherein the base filter and the first filter slice are each independently movable in and/or out of a beamline by a rotary motion axis.

4. The beam filter assembly of claim 1, wherein the base filter is configured to modify an energy spectrum of the x-ray beam produced when the radiation machine operates at the base energy level, and the first filter slice is stackable with the base filter when in use to modify an energy spectrum of the x-ray beam produced when the radiation machine operates at the first energy level.

5. The beam filter assembly of claim 1, wherein the base filter is configured to modify a dose distribution of the x-ray beam produced when the radiation machine operates at the base energy level, and the first filter slice is stackable with the base filter when in use to modify a dose distribution of the x-ray beam produced when the radiation machine operates at the first energy level.

6. The beam filter assembly of claim 1, further comprising a second filter slice stackable with the first filter slice and/or the base filter when in use to modify a beam quality of an x-ray beam produced when the radiation machine operates at a second energy level higher than the first energy level, wherein the second filter slice is independently movable in and out of the beam line.

7. The beam filter assembly of claim 6, wherein the second filter slice is configured to stack with the first filter slice and the base filter when in use to modify the beam quality of the x-ray beam produced when the radiation machine operates at the second energy level.

8. The beam filter assembly of claim 6, wherein the second filter slice is configured to stack with the base filter when in use to modify the beam quality of the x-ray beam produced when the radiation machine operates at the second energy level.

9. The beam filter assembly of claim 6, wherein the second filter slice is configured to stack with the first filter slice and/or the base filter when in use to modify an energy spectrum and/or a dose distribution of the x-ray beam produced when the radiation machine operates at the second energy level.

10. The beam filter assembly of claim 6, further comprising a third filter slice stackable with the second and first filter slices, and/or with the base filter when in use to modify a beam quality of an x-ray beam produced when the radiation machine operates at a third energy level higher than the second energy level, wherein the third filter slice is independently movable in and out of the beam line.

11. The beam filter assembly of claim 10, wherein the third filter slice is configured to stack with the second and first filter slices and the base filter when in use to modify the beam quality of the x-ray beam produced when the radiation machine operates at the third energy level.

12. The beam filter assembly of claim 10, wherein the third filter slice is configured to stack with the base filter when in use to modify the beam quality of the x-ray beam produced when the radiation machine operates at the third energy level.

13. The beam filter assembly of claim 10, wherein the third filter slice is configured to stack with the second and first filter slices, and/or with the base filter when in use to modify an energy spectrum and/or a dose distribution of the x-ray beam produced when the radiation machine operates at the third energy level.

14. The beam filter assembly of claim 10, further comprising a fourth filter slice stackable with the third, second, and first filter slices, and/or with the base filter to modify a beam quality of an x-ray beam produced when the radiation machine operates at a fourth energy level higher than the third energy level, wherein the fourth filter slice is independently movable in and out of the beam line.

15. The beam filter assembly of claim 14, wherein the fourth filter slice is configured to stack with the third, second and first filter slices, and the base filter when in use to modify the beam quality of the x-ray beam produced when the radiation machine operates at the fourth energy level.

16. The beam filter assembly of claim 14, wherein the fourth filter slice is configured to stack with the base filter when in use to modify the beam quality of the x-ray beam produced when the radiation machine operates at the fourth energy level.

17. The beam filter assembly of claim 14, wherein the fourth filter slice is configured to stack with the third, second and first filter slices, and/or with the base filter when in use to modify an energy spectrum and/or a dose distribution of the x-ray beam produced when the radiation machine operates at the fourth energy level.

18. The beam filter assembly of claim 14, wherein the base filter is configured to modify a beam quality of an x-ray beam produced when the radiation machine operates at the base energy level at about 4 MV, the first filter slice is configured to stack with the base filter when in use to modify a beam quality of an x-ray beam produced when the radiation machine operates at the first energy level at about 6 MV, the second filter slice is configured to stack with the first filter slice and the base filter when in use to modify a beam quality of an x-ray beam produced when the radiation machine operates at the second energy level at about 10 MV, the third filter slice is configured to stack with the second and first filter slices and the base filter when in use to modify a beam quality of an x-ray beam produced when the radiation machine operates at the third energy level at about 15 MV, and the fourth filter slice is configured to stack with the third, second, and first filter slices and the base filter when in use to modify a beam quality of an x-ray beam produced when the radiation machine operates at the fourth energy level at about 18 MV.

19. A beam filter assembly for use in a radiation machine capable of operating at various energy levels, the beam filter assembly, comprising:
  a base filter configured to modify a beam quality of an x-ray beam produced when the radiation machine operates at a base energy level; and
  a $1^{st}$ filter slice and N filter slices each being stackable with the base filter (N being an integer greater than 1 and less than or equal to 10), wherein the $1^{st}$ and N filter slices are configured such that
  the $1^{st}$ filter slice is for use at least in modifying an x-ray beam produced when the radiation machine operates at a $1^{st}$ energy level, a $2^{nd}$ filter slice for use at least in modifying an x-ray beam produced when the radiation machine operates at a $2^{nd}$ energy level, and in such successive order that an $(N-1)^{th}$ filter slice is for use at least in modifying an x-ray beam produced when the radiation machine operates at an $(N-1)^{th}$ energy level, and an $N^{th}$ filter slice for use at least in modifying an x-ray beam produced when the radiation machine operates at an $N^{th}$ energy level, and wherein the $N^{th}$ energy level is higher than the $(N-1)^{th}$ energy level, and in such successive order that the $2^{nd}$ energy level is higher than the $1^{st}$ energy level, and the $1^{st}$ energy level is higher than the base energy level; and
  wherein when an $M^{th}$ filter slice (M being an integer greater than 1 and less than or equal to N) is stacked with the base filter in use to modify an x-ray beam produced when the radiation machine operates at an $M^{th}$ energy level, the $1^{st}$ through $(M-1)^{th}$ filter slices are stacked between the $M^{th}$ filter slice and the base filter,
  wherein the N filter slices are each independently movable in and/or out of a beam line.

20. The beam filter assembly of claim 19, wherein the base filter and the N filter slices are each configured to modify an energy spectrum of an x-ray beam.

21. The beam filter assembly of claim 19, wherein the base filter and the N filter slices are each configured to modify a dose distribution of an x-ray beam.

22. The beam filter assembly of claim 19, wherein the base filter and N filter slices are each independently movable in and/or out of a beamline by a linear motion axis.

23. The beam filter assembly of claim 19, wherein the beam filter and N filter slices are each independently movable in and/or out of a beamline by a rotary motion axis.

24. The beam filter assembly of claim 19, wherein the $1^{st}$ and N filter slices are each configured to be used only in a combination including the base filter.

* * * * *